US00PP09068P

United States Patent [19]

Caudle et al.

[11] Patent Number: Plant 9,068

[45] Date of Patent: Mar. 7, 1995

[54] APPLE TREE: CAUDLE CULTIVAR

[75] Inventors: Darrel D. Caudle; Marilynn M. Caudle, both of Dryden, Wash.

[73] Assignee: Carousel Apple, Inc., Orando, Wash.

[21] Appl. No.: 114,957

[22] Filed: Aug. 31, 1993

[51] Int. Cl.[6] ..... A01H 5/00

[52] U.S. Cl. ..... Plt./34.1

[58] Field of Search ..... Plt. 34.1, 35, 35.1, Plt. 35.2

*Primary Examiner*—James R. Feyrer

*Attorney, Agent, or Firm*—Christensen, O'Connor, Johnson & Kindness

[57] ABSTRACT

A new variety of apple tree of unknown parentage, bearing apples of exceptional shelf life and keeping quality, exhibiting distinctive fruit coloration and shape, a long stem, large leaves, and unused bore shoot and bud extension.

5 Drawing Sheets

BACKGROUND AND ASEXUAL REPRODUCTION OF THE TREE

The subject plant is a new and distinct variety of apple tree that was discovered as a chance seedling of unknown parentage in the orchard of Darrel and Marilynn Caudle in Dryden, Wash. The original tree was found in a block of Red Delicious apple trees with Golden Delicious pollenizers in the same orchard. This new variety has been asexually reproduced, by bark graft and budding, and fruited through three successive generations in the discoverers' orchard. The characteristics of this variety have remained the same through three generations. The varietal name "Caudle Cultivar" is proposed for the subject apple tree.

SUMMARY OF THE TREE

This new variety of apple tree is distinguished from other known varieties by its fruit, which has a color pattern of red striping over a greenish-yellow background. The green-yellow ground color is identified, using Ridgeway's Color Standards and Nomenclature, as Plate V, color number 27 GY, Tone F Pale Green Yellow. The stripe color pattern varies between Nopal Red (Plate 1, color number 3 O-R, Tone I) to Ox Blood Red (Plate 1, color number 1 Red, Tone K). The lenticels on the apple are numerous, of medium size, the characteristically colored Sea Foam Yellow (Plate XXXI, color number 25 YGY, Tone F). The fruit generally resembles a Red Delicious apple in shape but is more roundish to conical; in addition, the five points, or lobes, are not as prominent as those of a Red Delicious Apple. The fruit stem of the new variety is slender and unusually long, typically one and one-half to one and three-quarters inches in length. These distinctive characteristics are all shown in FIG. 1.

This new variety is further distinguishable by its large leaves. As shown in FIG. 2, the leaf is larger than those of Red Delicious and Golden Delicious leaves.

This new variety of apple tree also exhibits an unusual growth of the bore shoot of leaves from the central column or pirostele that supports the flowers (and later the fruit). The bore shoot (shown at the arrow in FIG. 3) undergoes a distinctive extension in length during the blooming season. Bore shoots of this new variety at full bloom average two and one-half inches in length; while Red Delicious and golden Delicious bore shoots average two inches in length and one and one-quarter inches in length, respectively. FIG. 4 shows the bore shoot of this new variety as the apple matures.

This new variety of apple tree also exhibits an unusual bud extension. The bud extension, that is, the seasonal growth from the previous year's fruit bud to the principal flower stem, is elongated at full bloom in the subject tree (three-quarters to one inch) as compared to Red Delicious (one-quarter inch) and Golden Delicious (one-quarter to one-half inch) trees. Representative photographs of the bud extensions (taken approximately 80 days after full bloom) are shown in FIGS. 5A (the new variety), 5B (Red Delicious), and 5C (Golden Delicious).

Additional features of the subject apple trees are described in detail below.

DETAILED BOTANICAL DESCRIPTION OF THE "CAUDLE" TREE

Tree

Growth form: This new variety of apple tree has been observed growing on the following root stocks: seedling root stock, EMLA 111, and Malling 9 (NAKB 337). The subject trees are vigorous and tall, with a spreading, open growth form. Tree size of the original specimen at age 10 years is about 11 feet wide and 14 feet tall. Average terminal growth each year is approximately 14 to 20 inches. The trunk is medium (neither stocky nor slender), with smooth bark. The branches are medium (as opposed to slender or thick) and generally straight. The subject tree does not exhibit a propensity to form spurs; the spur branching characteristics are similar to a standard Golden Delicious tree. The bark of young trees is not a dark as that of Red Delicious trees but darker than the bark of Golden Delicious trees of comparable age. The color of one-year dormant wood is Dark Corinthian Purple (Plate XXXVIII-m). The mature bark is characteristically dull. Tree lenticels are numerous and of medium size. Lenticels on three-year-old wood are more horizontal than those on a standard Golden Delicious tree, which has lenticels that are more round in shape. The straight branchles tend to be medium-jointed with some zigzagging tendency observed. The epidermis is smooth and dull. Internodes are of medium length, about one to one and one-half inches, similar to standard Golden Delicious trees. Crotch angles are from about 30 to about 45 degrees from vertical.

Leaves: Buds are medium in size and length, and pointed (similar to Golden Delicious). Leaf scars are prominent, similar to Bisbee Red Delicious trees. The ovate leaves are distictively large: approximagely five and one-half inches in length and two and three-quarters inch wide. The leaves are thick, medium green in color (Ackermann's Green, Plate XVIII-k), and smooth. The color of the primary vein on the front side of the leaf is Light Grape (Plate XLI-b). The leaf margin is coarsely serrated. The petiole is of medium length (about one and one-half to about one and three-quarters inches) and thickness. The tomentum of the leaf blades are less pubescent than standard Golden Delicious leaves, and extremely less pubescent than Bisbee Red Delicious leaves.

Figure 1:
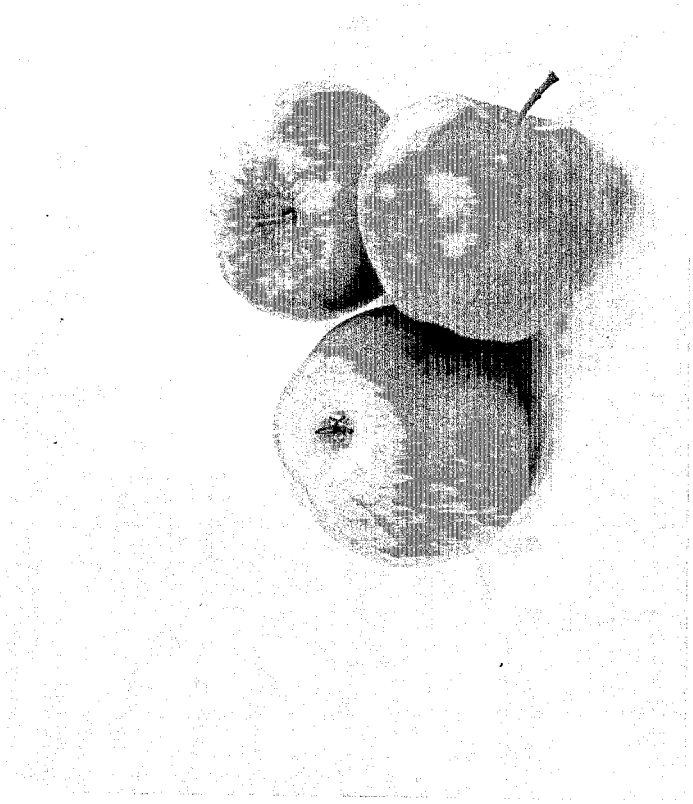
FIG. 1 shows three typical specimens of mature fruit from the Caudle Tree positioned such that the blossom end, stem end, and side view are revealed to reflect fruit shape.
Figure 2:
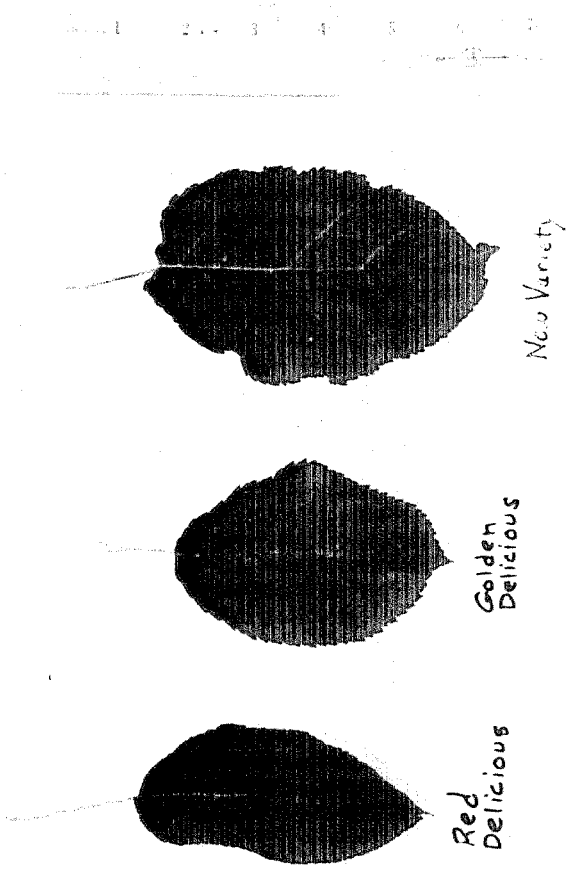
FIG. 2 depicts representative leaves from "Red Delicious," "Yellow Delicious," and "Caudle," respectively.
Figure 4:
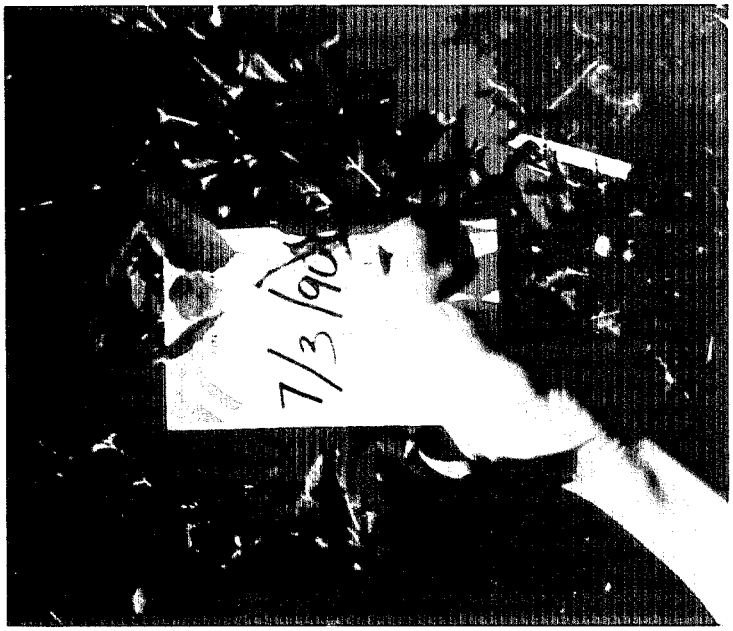
FIG. 4 shows the bore shoot at about mid growing season.
Figure 3:
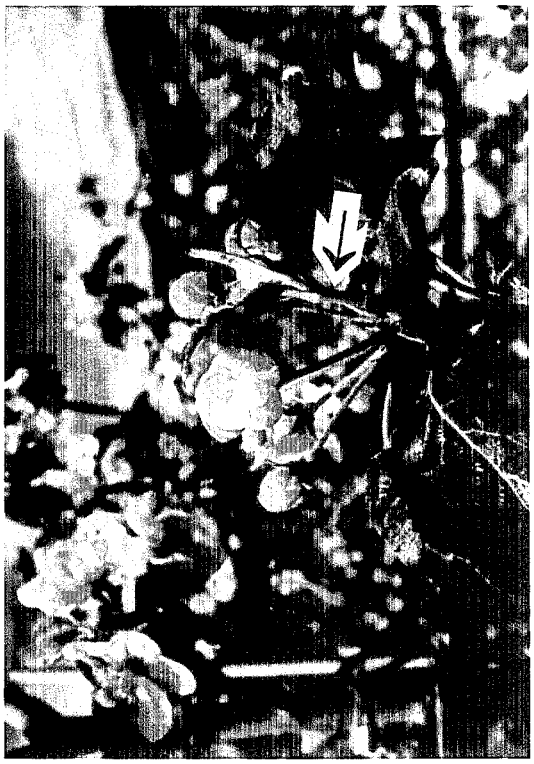
FIG. 3 illustrates the distinctive bore shoot of this tree in early season.
Figure 5A:
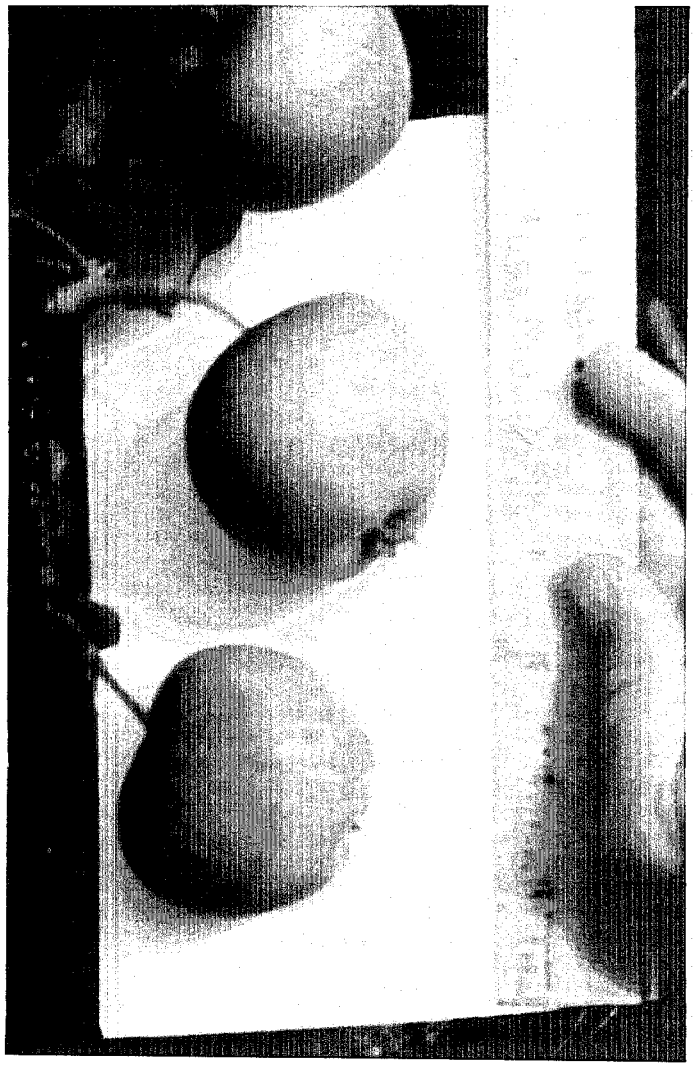
FIGS. 5A, 5B, and 5C compare the fruit and stems of "Caudle," "Red Delicious," and "Yellow Delicious" at about 80 days into the growing season after full bloom.
Figure 5B:
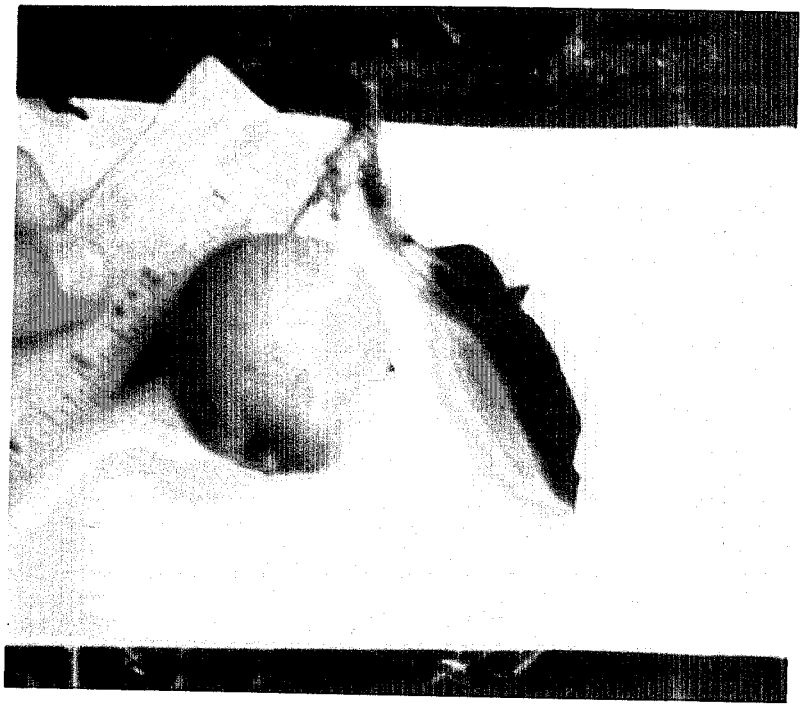
Figure 5C:
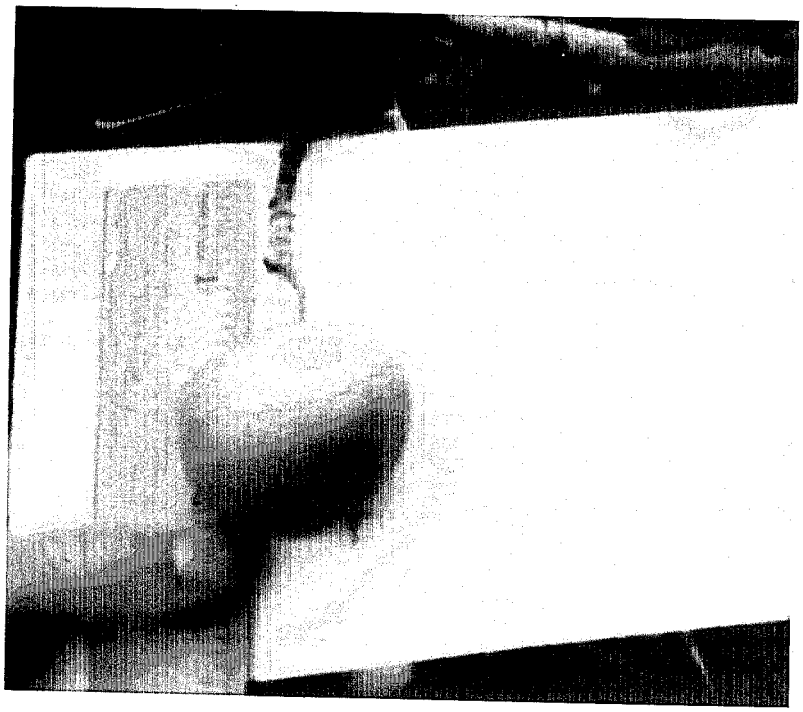

Flowers: The subject tree is characterized by large, showy flowers (FIG. 3). The closed flower is pink on the outside of the petals but opens to a mostly white flower. The flowers are fertile (i.e., self-fertile and will cross pollinate) and are generally distributed uniformly on the tree. If seed number is reduced without pollination, correspondingly size, type-length diameter ratio is affected, resulting in rounder fruit. The flower clusters are loosely arranged. The date of bloom is typically the same as adjacent Golden Delicious trees and follows that of adjacent Red Delicious trees by one day or so.

This new variety is a hardy, productive, and regular bearer. The new variety is more productive than Bisbee Red Delicious, and equal to standard Golden Delicious trees. Its susceptibilities to insects and diseases are similar to Red and Golden Delicious apple trees. The tree is not mildew resistant.

Fruit

The apples hang very well on the tree and typically ripen 155 to 165 days after full bloom. Thinning is required during heavy bloom years to produce premium-sized fruit. Thinning is required to produce uniform color and appearance. The apple of this new variety has less acid than standard Golden Delicious apples, and more acid than Bisbee Red Delicious apples, at optimum long-term controlled atmosphere harvest levels:

| | Pressure | Soluble Solids | Acid |
|---|---|---|---|
| Caudle | 16# | 12 | .400 |
| Golden Del. | 16# | 11 | .500 |
| Bisbee Del. | 17# | 10.3 | .270 |

Average fruit size at harvest with adequate thinning is 3.23 inches in diamter and 3.75 inches in length. The calyx basin averages ½ inch in depth and ¾ inch in width. The fruit has a closed calyx, and the calyx tube is small and long. The cavity at the stem end is approximately one inch deep and ¾ inch wide and is symmetrical. The stem length averages 1.45 inches. The cone area is medium in size and the halves are equal.

The apples are of best quality. The apples begin to take on stripes in mid-September and these improve until mid-October harvest. Comparable harvest dates are: Standard Golden Delicious harvest, September 10–20; Red Delicious harvest, Sep. 24-October 4; and Caudle Cultivar harvest, October 7–25. No. water core has been observed. Normal fruit size will average size 80–88, using USDA fruit grades. The apple skin is smooth, dull and of medium thickness and toughness. The apple bloom is very light. Skin is tougher than standard Golden Delicious, but not as tough as Bisbee Red Delicious. The basin of the fruit is more pointed than standard Golden Delicious, but not as Bisbee Red Delicious. The cavity is deeper and narower than standard Golden Delicious and Bisbee Red Delicious. The flesh is white, firm, crisp, and juicy, with a characteristic subacid, aromatic flavor. The fruit is less susceptible to russet than standard Golden Delicious. The shelf life and keeping quality of the apple are exceptional and greatly exceed those of both Red Delicious and Golden Delicious apples. The apple is dessert quality, comparable with Red Delicious and Golden Delicious, and has a longer storage capability.

We claim:

1. A new and distinct variety of apple tree substantially as shown and described.

* * * * *

3/5

UNITED STATES PATENT AND TRADEMARK OFFICE

CERTIFICATE OF CORRECTION

PATENT NO. : Plant 9,068

DATED : March 7, 1995

INVENTOR(S) : D.D. Caudle et al.

It is certified that error appears in the above-indentified patent and that said Letters Patent is hereby corrected as shown below:

On title page,

After "[58]" Insert --[56] References Cited
U.S. Patent Documents
PP 6588 2/1989 Hauenstein .... PLT./34.1--

| Column | Line | |
|---|---|---|
| 3 | 27 | "Grape (Plate XLI-b)." should read --Grape Green (Plate XLI-b).-- |
| 4 | 19 | "diamter" should read --diameter-- |

Signed and Sealed this

Sixth Day of June, 1995

*Attest:*

*Attesting Officer*

BRUCE LEHMAN

*Commissioner of Patents and Trademarks*